(12) United States Patent
Hahn (10) Patent No.: US 8,702,699 B2
(45) Date of Patent: Apr. 22, 2014

(54) MEDICAL INSTRUMENT

(75) Inventor: Martin Hahn, Boll (DE)

(73) Assignee: Karl Storz GmbH & Co. KG (DE)

( * ) Notice: Subject to any disclaimer, the term of this patent is extended or adjusted under 35 U.S.C. 154(b) by 1651 days.

(21) Appl. No.: 11/503,105

(22) Filed: Aug. 11, 2006

(65) Prior Publication Data

US 2007/0038215 A1 Feb. 15, 2007

(30) Foreign Application Priority Data

Aug. 12, 2005 (DE) .......................... 10 2005 039 106

(51) Int. Cl.
*A61B 18/14* (2006.01)
*A61B 1/018* (2006.01)

(52) U.S. Cl.
USPC ........................................... 606/46; 600/104

(58) Field of Classification Search
USPC .......... 606/41, 46, 50–52; 600/102, 104–106, 600/114
See application file for complete search history.

(56) References Cited

U.S. PATENT DOCUMENTS

| | | | |
|---|---|---|---|
| 3,939,840 A * | 2/1976 | Storz | 606/46 |
| 4,068,667 A * | 1/1978 | Iglesias | 606/46 |
| 4,744,361 A | 5/1988 | Karasawa | 128/303.15 |
| 5,007,907 A * | 4/1991 | Nishigaki et al. | 606/46 |
| 5,014,708 A * | 5/1991 | Hayashi et al. | 600/436 |
| 5,024,212 A * | 6/1991 | Bonnet et al. | 600/119 |
| 5,112,329 A * | 5/1992 | Storz | 606/46 |
| 5,857,962 A | 1/1999 | Bracci et al. | 600/105 |
| 5,885,277 A | 3/1999 | Korth | 600/35 |
| 5,919,191 A * | 7/1999 | Lennox et al. | 606/48 |
| 5,925,040 A * | 7/1999 | Nardella et al. | 606/41 |
| 5,993,445 A | 11/1999 | Issa | 606/46 |
| 6,033,404 A * | 3/2000 | Melzer et al. | 606/46 |
| 6,113,594 A * | 9/2000 | Savage | 606/41 |
| 6,358,200 B1 | 3/2002 | Grossi | 600/156 |
| 6,746,395 B2 * | 6/2004 | Brommersma et al. | 600/105 |
| 6,918,909 B2 * | 7/2005 | Ohyama et al. | 606/46 |
| 7,169,147 B2 * | 1/2007 | Nosel | 606/46 |
| 2003/0144661 A1* | 7/2003 | Brommersma et al. | 606/46 |
| 2004/0064139 A1 | 4/2004 | Yossepowitch | 606/46 |
| 2004/0082938 A1* | 4/2004 | Ohyama et al. | 606/1 |
| 2004/0242959 A1* | 12/2004 | Nosel | 600/105 |
| 2005/0070893 A1 | 3/2005 | Aue et al. | 606/46 |

FOREIGN PATENT DOCUMENTS

| | | |
|---|---|---|
| DE | 37 16 359 C2 | 11/1987 |
| DE | 42 42 143 A1 | 6/1994 |
| DE | 44 25 015 | 1/1996 |
| DE | 196 30 666 | 11/1997 |
| DE | 103 45 111 A1 | 5/2005 |
| EP | 0 084 419 | 7/1983 |

OTHER PUBLICATIONS

European Search Report, Dec. 14, 2006, 6 pages.

* cited by examiner

*Primary Examiner* — Michael Peffley
*Assistant Examiner* — Samantha Good
(74) *Attorney, Agent, or Firm* — St. Onge Steward Johnston & Reens LLC (57) ABSTRACT

A medical instrument, in particular a resectoscope, comprises a distal first work element which is used for treating body tissue and which can be connected via an elongate work element holder to a handle at a proximal end for moving the work element, the handle having a carriage which is movable in the longitudinal direction of the work element holder and which has a first seat for releasable attachment of the work element holder to the carriage, and further comprises a receiver for an endoscope whose endoscope shaft, in the assembled state, extends substantially parallel to the first work element holder. The carriage has at least a second seat which is spaced apart from the first seat and provided for the first work element holder, or at least a second work element holder which at the distal end supports at least a second work element.

11 Claims, 8 Drawing Sheets

MEDICAL INSTRUMENT

CROSS-REFERENCE TO RELATED APPLICATION

The present application claims priority of German patent application No. 10 2005 039 106.0 filed on Aug. 12, 2005.

BACKGROUND OF THE INVENTION

The invention relates to a medical instrument, in particular resectoscope comprising a first work element for treating body tissue, which can be connected via an elongate work element holder to a handle at a proximal end for moving the work element, the handle having a movable carriage which has a first seat for releasable attachment of the work element holder to the carriage, and comprising a receiver for an endoscope whose endoscope shaft, in the assembled state, extends substantially parallel to the first work element holder.

A medical instrument of the abovementioned type is used in minimally invasive surgery, particularly in the field of urology. In urology, such an instrument is used to dissect tissue, in particular to cut tissue, in the urethra for example. Such an instrument is also known as a resectoscope, although the present invention is not limited to a resectoscope. The instrument is usually combined with an endoscope.

An instrument known from the document DE-A-103 45 111 has, as its work element, an electrode which is mounted on an electrode holder, which acts as work element holder, at the distal end. The electrode itself is, for example, in the form of a resection loop. With such an electrode, for example in the form of a resection loop, tissue is cut with a tractive action under the effect of high-frequency current applied to the electrode. However, under the effect of high-frequency current, such an electrode can work not only with a cutting action but also, if suitably configured, with a coagulating or vaporizing action. The stated document describes how, instead of using work elements that can be acted on by high-frequency current, it is also possible to use instruments that operate without current, for example blades, curettes, etc.

In the known instrument, the proximal end is provided with a handle which has a carriage comprising a seat for receiving the proximal end of the work element holder. In the case where the work element holder supports an electrode at the distal end, the proximal end of the work element holder on the carriage additionally has a electrical contact arrangement, that is to say, in the assembled state, is electrically conductively connected to the terminal for a power supply cable.

In instruments of this kind, it is customary to provide a plurality of different work elements, each with their respective work element holder, which are interchanged by the physician as and when desired and can be secured in the seat of the carriage. Depending on the preference of the physician using the instrument, it is sometimes preferred to cut tissue with an electrode, that is to say using high-frequency current, or to cut it in a purely mechanical way without current, for example with a blade. If, for example, a blade that operates without current is to be used instead of the electrode for cutting tissue, the electrode and its work element holder (electrode holder) in the known instrument are released from the carriage and then removed, and the blade with its work element holder is secured in the same seat on the carriage. This means that all the different work elements available, and the work element holders connected to them, are always secured at the same site on the carriage. Thus, the position of the work element at the distal end of the work element holder, which position is determined by the shape of the work element and of the work element holder, is at all times fixed, in particular the position of the work element relative to the distal viewing window of the endoscope and, therefore, relative to the viewing field of the endoscope. Therefore, if it is desired to be able to use the same work element, for example a blade or a resection loop, in different spatial positions, in particular with respect to the viewing field of the endoscope, it is necessary, in the known instrument, to store the same type of work element, for example a resection loop, in a plurality of different geometric configurations of the work element and of the work element holder. This, however, increases the cost of such an instrument.

The document DE-A-42 42 143 discloses a high-frequency, multi-functional hand-held surgical instrument for bipolar coagulation and cutting and also for irrigation of the operating site and suctioning of fluid and tissue sections in endoscopic interventions, said instrument being able to be connected to a high-frequency generator and to irrigation and suction means. In this known instrument, a high-frequency coagulation probe with two coagulation electrodes, and a high-frequency cutting probe with a cutting needle or cutting loop and with an insulated counter-electrode, can be secured at the same time on the instrument. The two high-frequency probes are each assigned a slide on the handle of the instrument, so that the two probes can be alternately and individually moved in the axial direction, in order to carry out a treatment procedure. The document does not disclose how the two probes are secured on the slides.

SUMMARY OF THE INVENTION

The object of the present invention is to improve the function of a medical instrument of the type mentioned at the outset, as far as possible without incurring increased costs.

According to an aspect of the invention, a medical instrument, in particular resectoscope, is provided, which comprises an elongate shaft having a distal end, a proximal end and defining a longitudinal direction. A handle is arranged at the proximal end of the shaft, and has a carriage movable in the longitudinal direction. The carriage has a first seat. An elongate first work element holder has a distal end and a proximal end, a first work element being arranged at the distal end of the first work element holder, and the proximal end of the first work element holder is releasably connectable with the first seat of the carriage of the handle. A receiver for receiving an endoscope has an endoscope shaft extending substantially parallel to the work element holder. The carriage has at least a second seat which is spaced apart from the first seat and provided for at least one of the first work element holder and at least a second work element holder supporting at least a second work element.

In the instrument according to the invention, it is therefore possible to secure one and the same work element holder with one and the same work element alternately in the first seat or in the at least second seat or in each additionally provided seat, as a result of which the physician is able to choose what is for him the most favourable spatial position of the work element at the distal end, in particular with respect to the viewing field of the endoscope. It is also possible, however, to use the first seat for a first type of work element, for example for work elements that can be operated by high-frequency current, and to use the at least second seat or additionally provided seats for another type of work element, in particular for work elements that operate without a current supply, for example blades, curettes and the like. By providing at least a second seat on the carriage, the function of the instrument according to the invention is ensured without appreciably higher costs. The fact that the at least second seat is likewise provided on the carriage, which is movable by actuating the handle for moving the work element at the distal end, means that the actuating mechanism which is already present for the carriage is advantageously also used for the at least second seat, as a result of which no additional construction costs are incurred in providing an actuating device for the at least second seat.

In a preferred embodiment, the first seat of the carriage is provided with an electrical contact arrangement, and the at least second seat of the carriage is electrically insulated relative to the first seat and has no electrical contact arrangement.

The advantage of this measure is that the carriage has least one seat which is provided for the attachment of a work element operating without current supply, for example a blade, and which is electrically insulated. In the known instrument, by contrast, one and the same seat is provided both for powered and also unpowered work elements, thus entailing the risk of current inadvertently also being applied to the unpowered work elements, which would pose a danger to the physician operating the instrument or to the patient. In the instrument according to the invention, this danger is advantageously avoided by provision of at least one electrically insulated seat without electrical contact arrangement.

In an advantageously simple manner from the design point of view, the at least second seat of the carriage is insulated relative to the first seat of the carriage by means of an electrically insulating plastic.

In another preferred embodiment, a particularly cost-effective design of the carriage with the at least two seats is achieved by the fact that the carriage as a whole is designed as a plastic body in which one or more electrical contacts are present in the first seat.

By producing the carriage as a whole as a plastic body with, for example, embedded electrical contacts in the first seat, it is possible, in an advantageously simple design, to ensure that the electrical insulation between the at least two seats is a reliable one and is secure against flashover.

While it is possible, in the context of the present invention, for the first and at least second seat on the carriage to be spaced apart at any desired positions relative to one another, another preferred embodiment entails that the first and at least second seat on the carriage are positioned such that, when the instrument is held in the hand in a due manner, the first seat is located above a receiving tube for the endoscope shaft, and the at least second seat is located below the receiving tube for the endoscope shaft.

"Above the receiving tube for the endoscope" and "below the receiving tube for the endoscope" does not necessarily mean here that the at least two seats for the first and/or second work element holder are arranged at axially the same or approximately the same level, and instead the seats for the work element holder or work element holders can be axially offset relative to the seat for the endoscope.

Since the work elements used in particular in resectoscopes, whether work elements powered by current or working without current, are designed such that a drawing cut can be performed with them, the work element thus being arranged substantially perpendicular to the pulling direction and thus to the direction of the work element holder or work element holders, the aforementioned measure has the advantage that the work element holder or work element holders in this position can be arranged completely outside the viewing field of the endoscope, and it is basically only the distal work element that can be seen in the viewing field of the endoscope.

In other words, this configuration means that the work element holder or work element holders do not obstruct the view through the endoscope to the treatment site.

In a more detailed form of the aforementioned feature, provision is preferably made that, when the instrument is held in the hand in a due manner, the first work element holder, in the state when secured on the carriage, extends above the endoscope shaft, and the first work element protrudes downward from the work element holder, approximately perpendicular to the longitudinal direction of the first work element holder.

This orientation of the work element and work element holder is preferably provided for an instrument powered by current supply, in which the work element is accordingly designed as an electrode, particularly in the form of a loop.

By contrast, for work elements that operate without a current supply, for example a blade, it is preferable that, when the instrument is held in the hand in a due manner, the at least second work element holder, in the state when secured on the carriage, extends below the endoscope shaft, and the at least second work element protrudes upward from the work element holder, approximately perpendicular to the longitudinal direction of the second work element holder.

In both cases, it is basically only the work element itself that can be seen in the viewing field of the endoscope, i.e. the resection loop or the blade, and the associated work element holders do not obstruct the view of the treatment site.

In another preferred embodiment, the first seat and/or the at least second seat of the carriage has/have a lock mechanism for securing the first or at least second work element holder.

This measure, known per se, also proves advantageous when the carriage has more than one seat for attachment of a work element holder.

In this connection, it is preferable if the first seat and the at least second seat each have a lock mechanism, and the latter are jointly assigned a common operating element for releasing the first and at least second work element holder.

In practice, the instrument according to the invention is used at any one time with only one work element, i.e. only one work element holder is secured at any one time in one of the seats of the carriage. For a structurally simple and cost-effective design, it is therefore advantageous if one operating element is provided with which the lock mechanisms of all the provided seats can be released at the same time, since in any case a work element holder is secured only in one seat.

In another preferred embodiment, a shaft can also be secured on the handle and, in the secured state, this shaft surrounds the first or at least second work element holder, and the carriage is axially movable relative to said shaft.

The shaft has the advantage that the instrument can be inserted more easily into natural orifices and into the treatment site, especially since in the elongate work element holders provided in such instruments are very thin and therefore relatively flexible, which makes it difficult to insert the work element holders, with the work element at the front, into the operating site.

In another preferred embodiment, the carriage is mounted in an axially movable manner on a guide tube, the guide tube serving as a receiving tube for the endoscope shaft.

In the medical instrument according to the invention, which at the same time has enhanced functionality on account of the presence of several seats for one or more work element holders, this measure, which is also known per se, leads to an advantageously simple design that requires few parts.

Further advantages and features will become evident from the following description of the attached drawing.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

An illustrative embodiment of the invention is shown in the drawing and is described in detail below with reference to said drawing, in which.

DETAILED DESCRIPTION OF AN EXEMPLARY EMBODIMENT

In FIGS. 1 to 8, general reference number 10 designates a medical instrument in the form of a resectoscope which is preferably used in minimally invasive operations in the field of urology. The instrument 10 can be used in particular for cutting prostate tissue.

In FIGS. 1 to 4, the instrument 10 is shown in a first operating mode in which it can be employed as an electrosurgical instrument. In this operating mode, the aforementioned tissue can be treated with the instrument 10 under the effect of high-frequency current.

In the operating mode in FIGS. 5 to 8, the instrument 10 is an instrument that is used without current, i.e. as an instrument with which the aforementioned tissue can, for example, be cut purely mechanically.

The instrument 10 will first be described in the aforementioned first operating mode and with reference to FIGS. 1 to 4.

Figure 1:
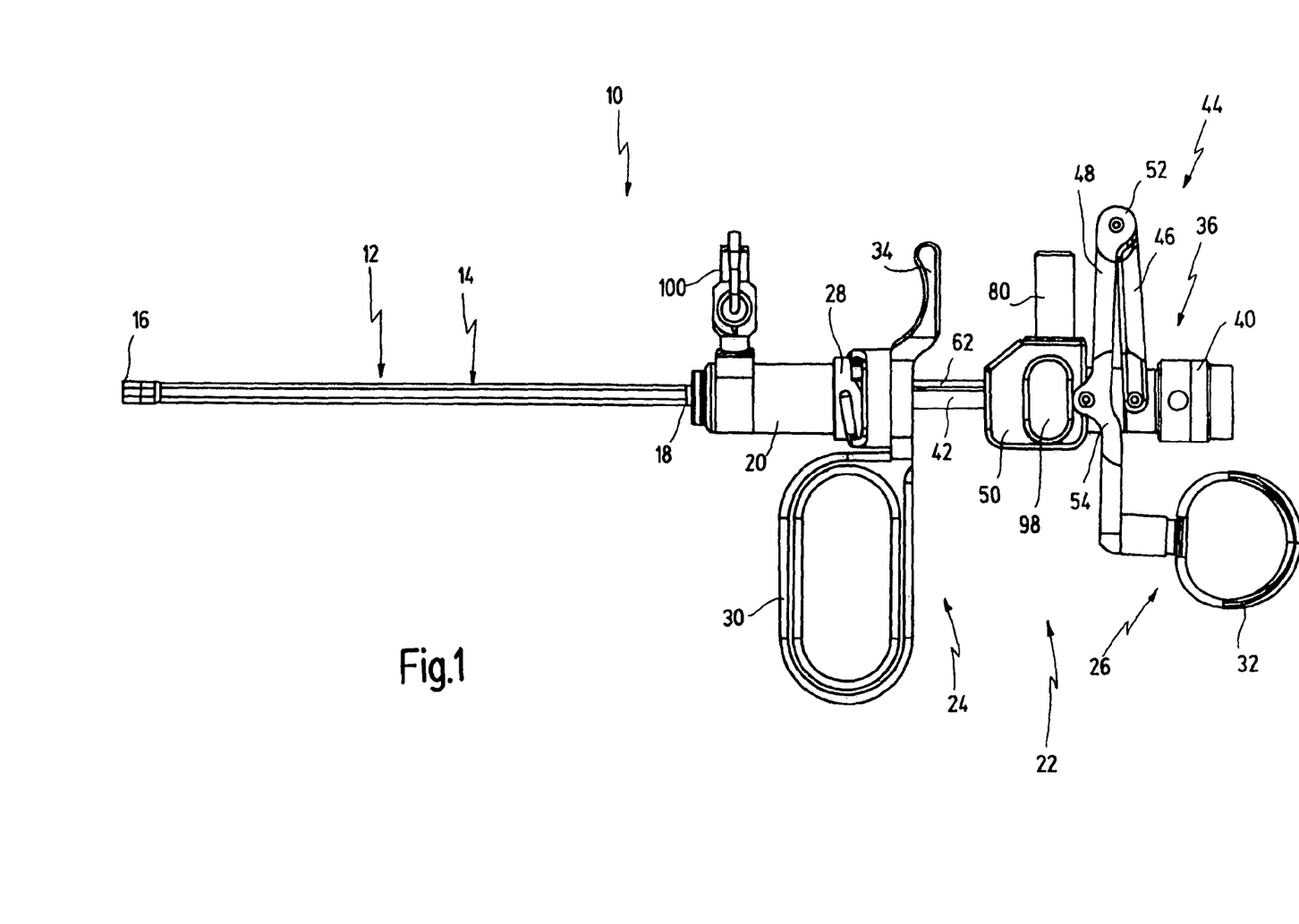
FIG. 1 shows an overall representation of a medical instrument in a first operating mode, seen in a side view.
Figure 2:
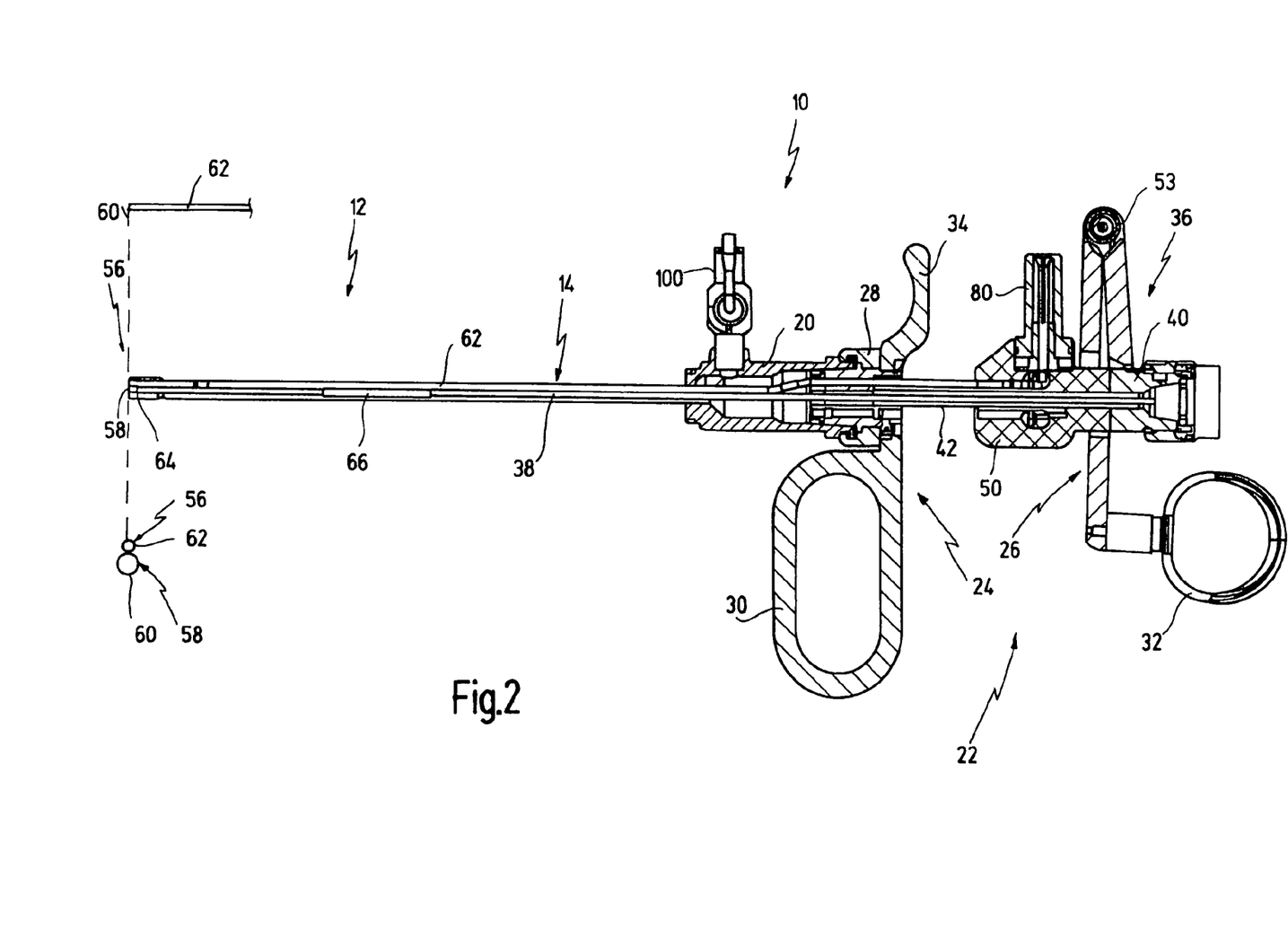
FIG. 2 shows the instrument from FIG. 1 in longitudinal section.

The instrument 10 has an elongate shaft 12 which is designed as a hollow tube 14 open at both ends. The hollow tube 14 has a distal end 16 and a proximal end 18. The proximal end 18 of the hollow tube 14 is fixedly connected to a coupling sleeve 20 of greater diameter.

In the proximal direction from the shaft 12, the instrument 10 has a handle 22 which comprises an immovable grip part 24 and a movable grip part 26. "Immovable" means that the grip part 24 is immovable relative to the shaft 12, and "movable" means that the grip part 26 is movable relative to the shaft 12. The shaft 12 is connected via the coupling sleeve 20 and a bayonet catch 28 to the handle 22, more precisely to the immovable part 24, and it can accordingly be detached from the handle 22 by releasing the bayonet catch 28.

The immovable part 24, which is arranged in the distal direction from the movable grip part 26, has a ring 30 for inserting the middle finger and ring finger, and the movable grip part 26 has a ring 32 for inserting the thumb. On the immovable grip part 24 there is also an extension 34 which serves to support the index finger of the same hand in which the handle 22 is gripped when the instrument 10 is being used correctly.

Figure 3:
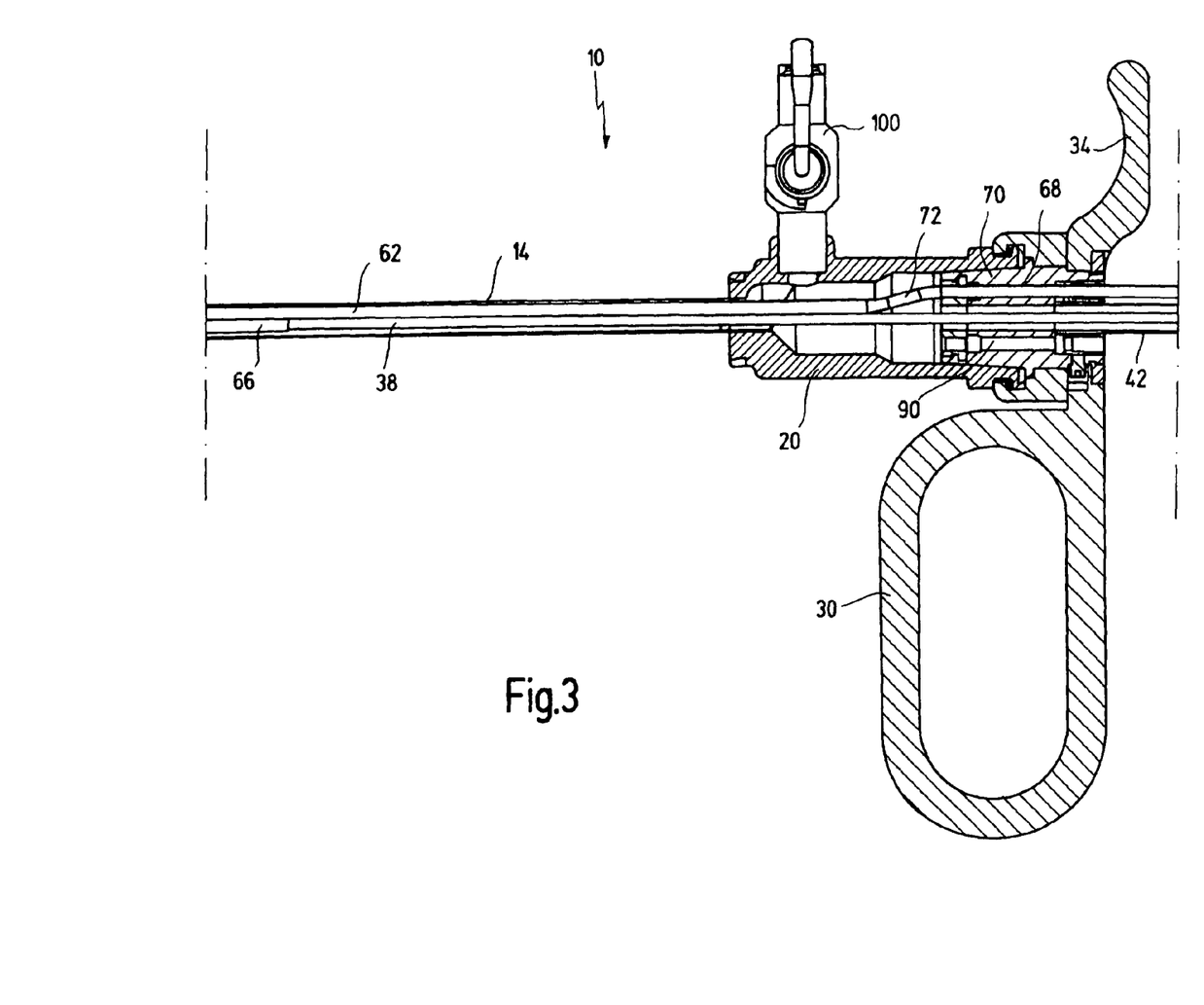
FIG. 3 shows an enlarged view of a detail of the instrument in FIGS. 1 and 2, in longitudinal section.
Figure 4:
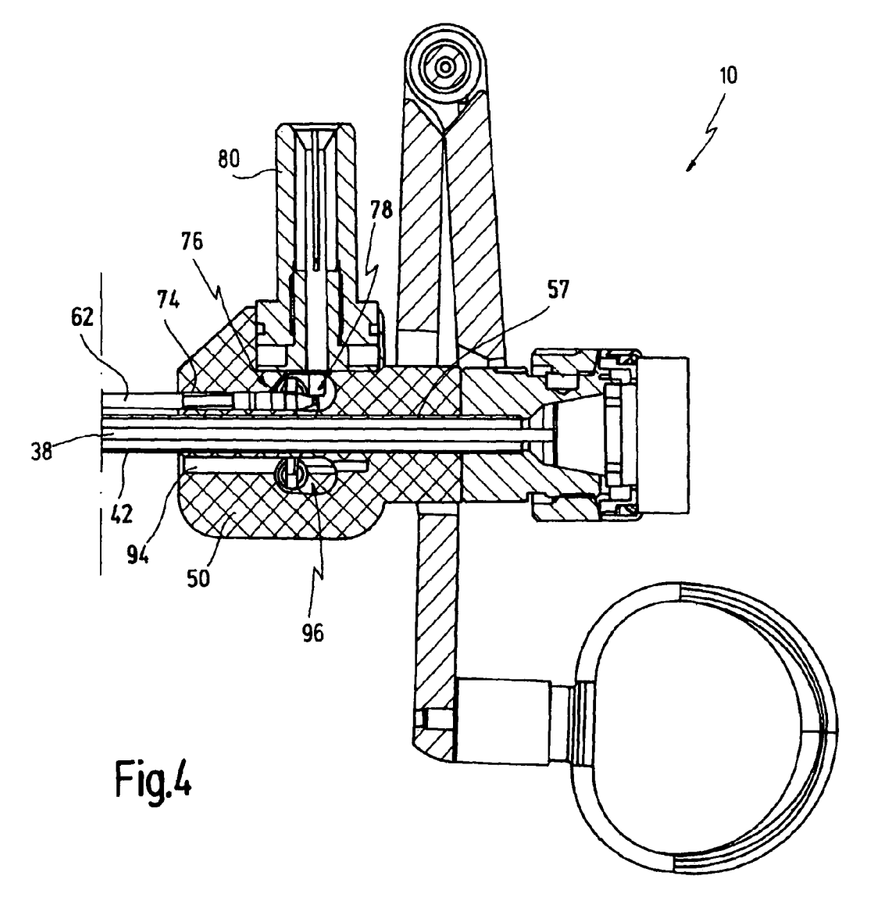
FIG. 4 shows an enlarged view of another detail of the instrument in FIGS. 1 and 2, in longitudinal section.

A receiver 36 for an endoscope is also immovable relative to the shaft 12, of which endoscope FIGS. 2 to 4 show only an endoscope shaft 38 which, when fitted on the instrument 10, extends from the proximal end of the instrument 10 to about the distal end 16 or close to the distal end 16 of the hollow tube 14. An eyepiece present at the proximal end of such an endoscope, or a fixture for attachment of a video camera, are not shown in the drawing.

At its proximal end, the receiver 36 for the endoscope has a coupling 40 for securing the endoscope on the instrument 10. Starting from the coupling 40, the receiver 36 has a receiving tube 42 which, according to FIG. 2, is fixedly connected to the immovable grip part 24, so that the coupling 40 of the receiver 36 is also fixedly connected to the immovable grip part 24 and thus immovable relative to the shaft 12.

An articulated lever arrangement 44 comprising a first articulated lever 46 and a second articulated lever 48, connects the movable grip part 26 to the receiver 36 for the endoscope and also to a carriage 50. For this purpose, the articulated lever 46 is articulated on the receiver 36 in the distal direction from the coupling 40, is connected to the articulated lever 48 via a hinge 52, while the articulated lever 48 is articulated on the carriage 50 via a hinge 54.

The carriage 50 is mounted so as to be axially movable on the receiving tube 42 as guide tube, in the longitudinal direction of said receiving tube 42. For this purpose, the carriage 50 has, according to FIG. 4, a continuous longitudinal bore 57 through which the receiving tube 42 extends. The carriage 50 is thus slidably displaceable on the receiving tube 42.

In FIGS. 1, 2 and 4, the carriage 50 is shown in its maximum proximal position. In this position, the grip parts 24 and 26 of the handle 22 are spaced apart from one another by the maximum extent. By moving the movable grip part 26 in the direction toward the immovable grip part 24, the carriage 50 is displaced distally on the tube 42, the distal end position of the carriage 50 being defined by its coming into abutment on the immovable grip part 24. The grip part 26 is also pretensioned into its proximal end position according to FIGS. 1, 2 and 4 via a torsion spring 53 (FIG. 2) in the hinge 52.

In the operating mode according to FIGS. 1 to 4, the instrument 10 also has a first work element 56 which is designed as an electrode 58 that can be operated with high-frequency current. In the present illustrative embodiment, the electrode 58 is designed as a resection loop 60 which, for purposes of illustration in FIG. 2, is shown in a side view in the upper half and in a front view in the lower half. The work element 56 is releasably connected to the carriage 50 via a work element holder 62 which extends from the work element 56 and runs in the longitudinal direction through the shaft 12 and parallel to the endoscope shaft 38 as far as the carriage 50. In the maximum proximal position of the carriage 50 depicted in FIGS. 1 and 2, the work element 56 lies approximately at the distal end 16 of the hollow tube 14 of the shaft 12 in front of the viewing window 64 of the endoscope shaft 38.

The work element holder 62 is designed in the form of a thin rod which is guided axially on the more rigid endoscope shaft 38 via a guide sleeve 66 which is fixedly connected to the work element holder 62 and through which the endoscope shaft 38 extends. Since the work element holder 62 is connected to the carriage 50, as will be described in more detail below, actuation of the movable grip part 26 by axial displacement of the carriage 50 leads to a displacement of the work element holder 62 and thus of the work element 56 in the longitudinal direction of the shaft 12 relative to the endoscope shaft 38 and the shaft 12.

Since the work element 62 is designed as an electrode 58, the work element 62 is designed to be electrically conductive, said work element holder 62 being accordingly insulated externally.

According to FIG. 3, the work element holder 62 is guided through the coupling sleeve 20 and a first bore 68 of a bushing 70 that is fixedly connected to the immovable grip part 24. Before the entry into the bore 68, the work element holder 62 has a kink 72. According to FIG. 4, the work element holder 62 extends from the bushing 70, parallel to the receiving tube 42 for the endoscope, to the carriage 50 which has a first seat 74 designed in the form of a bore that is basically shaped as a blind hole. The proximal end of the work element holder 62 is secured in the first seat 74, specifically by means of an automatically closing lock mechanism 76. By release or disengagement of the lock mechanism 76, the work element 56 fixedly connected to the work element holder 62 can be separated from the carriage 50 and removed.

To secure the work element holder 62 on the carriage 50, the proximal end of the work element holder 62 is simply fitted into the seat 74 until the lock mechanism 76 automatically locks shut. For this purpose, the lock mechanism 76 has, in a manner not shown here, a spring-loaded ram which is forced away via a bevelled surface at the proximal end of the work element holder 62 until the ram engages in a cutting at the proximal end of the work element holder 62.

The first seat 74 also has an electrical contact arrangement 78 which comprises one or more electrical contacts serving to electrically contact the work element holder 62 in the area of its proximal end. The carriage 50 for this purpose also has a connector 80 for connecting a power cable (not shown) via which the instrument 10 can be linked to a high-frequency current or voltage source. The connector 80 moves along with the movement of the carriage 50.

By applying high-frequency current to the loop 60 by actuating the movable grip part 26, a tractive cut can be made with the resection loop 60 under the effect of high-frequency current.

The first seat 74 is located on the carriage 50 above the receiving tube 42 for the endoscope when the instrument 10 is held duly in the hand when carrying out a treatment procedure. This position corresponds to the view of the instrument 10 in FIGS. 1 to 4. To put it another way, in relation to the endoscope shaft 38 and its longitudinal central axis, the first seat 74 is arranged at that end of the endoscope shaft 38 directed away from the grip parts 24 and 26.

The work element holder 62 extends along its entire length above the endoscope shaft 38, and the work element 56 in the form of the electrode 58 protrudes downward from the work element holder 62, approximately perpendicular to the work element holder 62, so that basically only the electrode 58 in the form of the resection loop 60 is to be seen in the viewing field of the endoscope through the viewing window 64.

In FIGS. 5 to 8, the instrument 10 is shown in a second operating mode in which the work element 56 and work element holder 62 are detached from the instrument 10, while a second work element 82 is now mounted on the instrument 10 and secured on the carriage 50 via a second work element holder 84.

Figure 5:
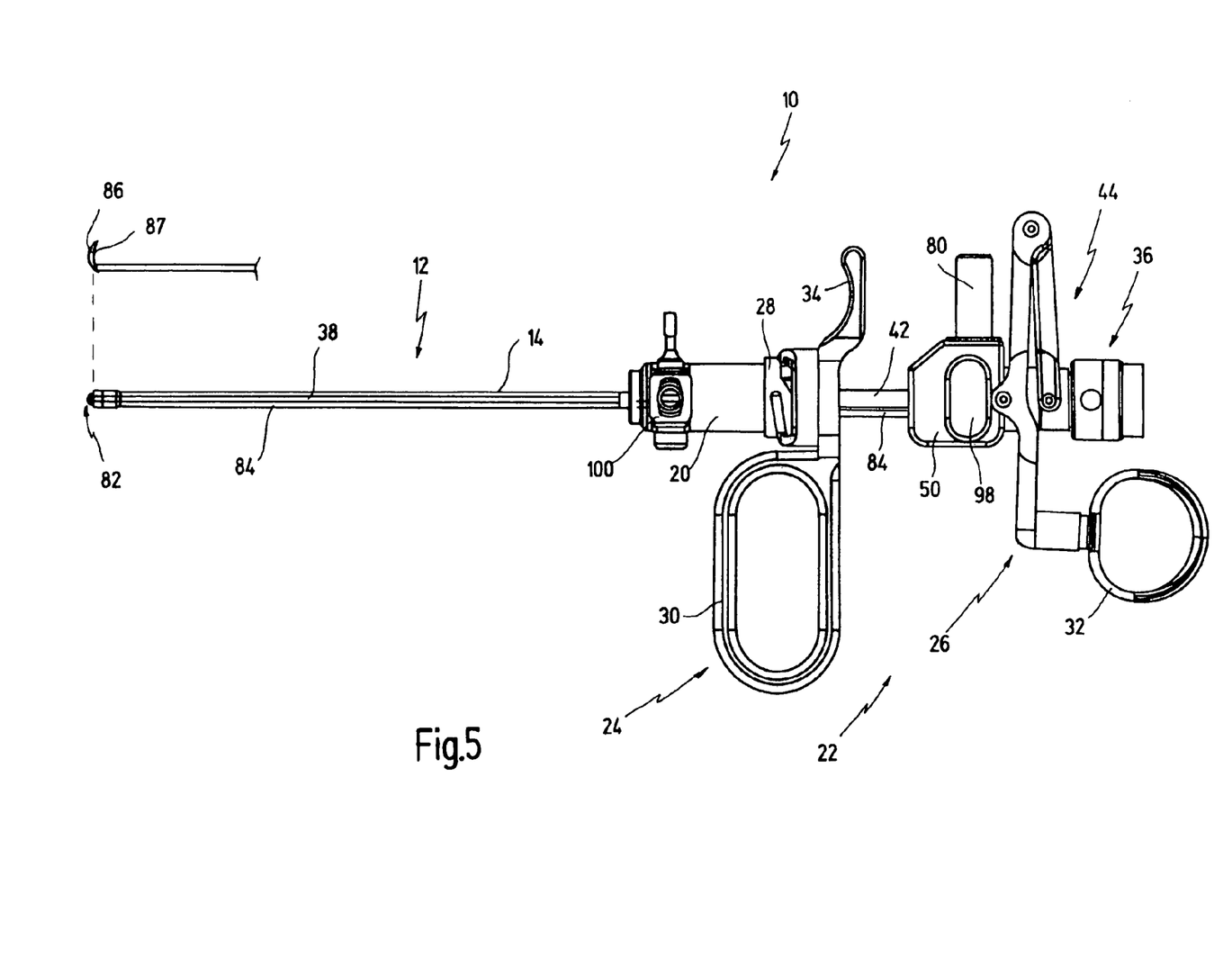
FIG. 5 shows an overall representation of the instrument in FIG. 1 in a second operating mode, seen in a side view.
Figure 6:
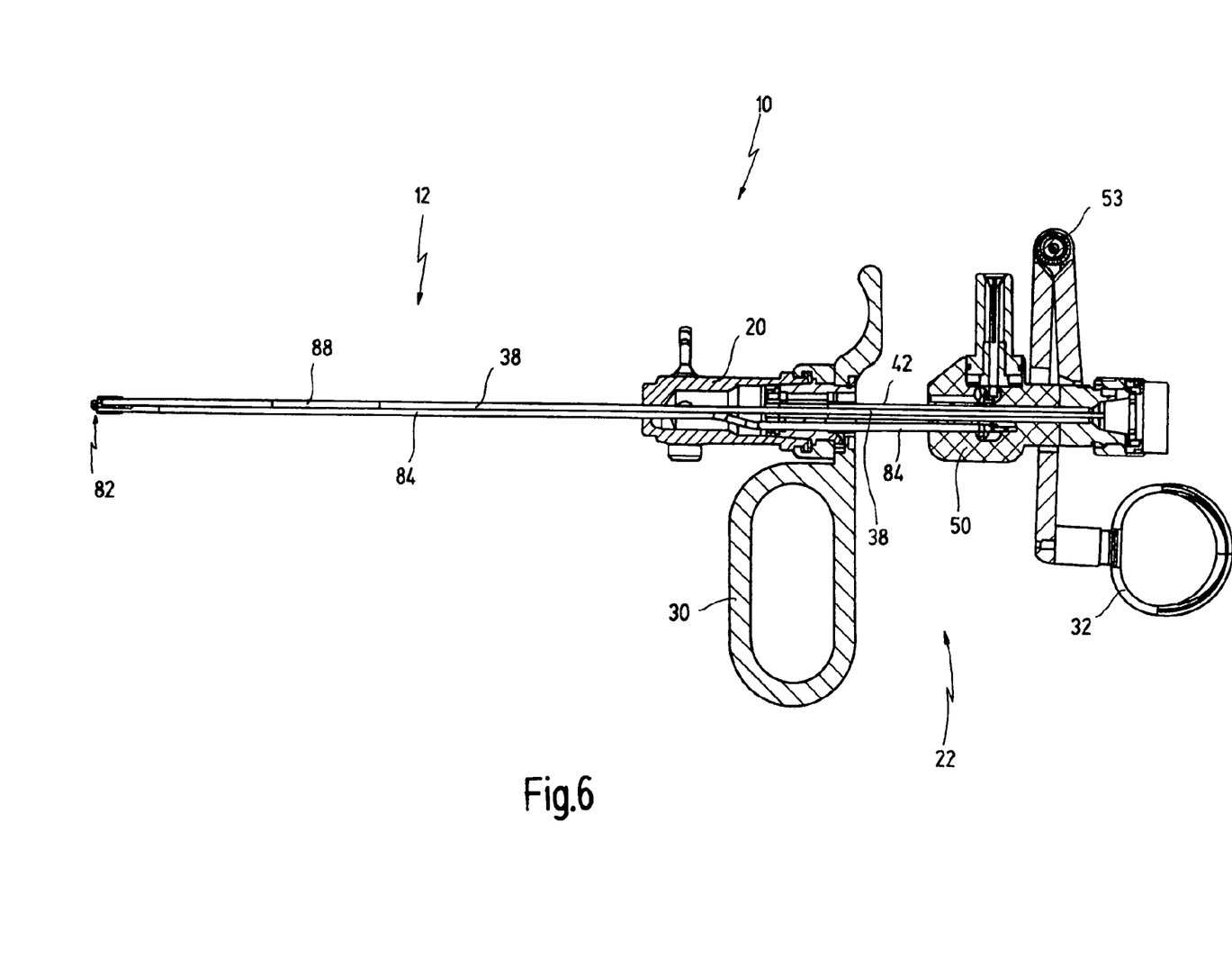
FIG. 6 shows the instrument from FIG. 5 in longitudinal section.
Figure 7:
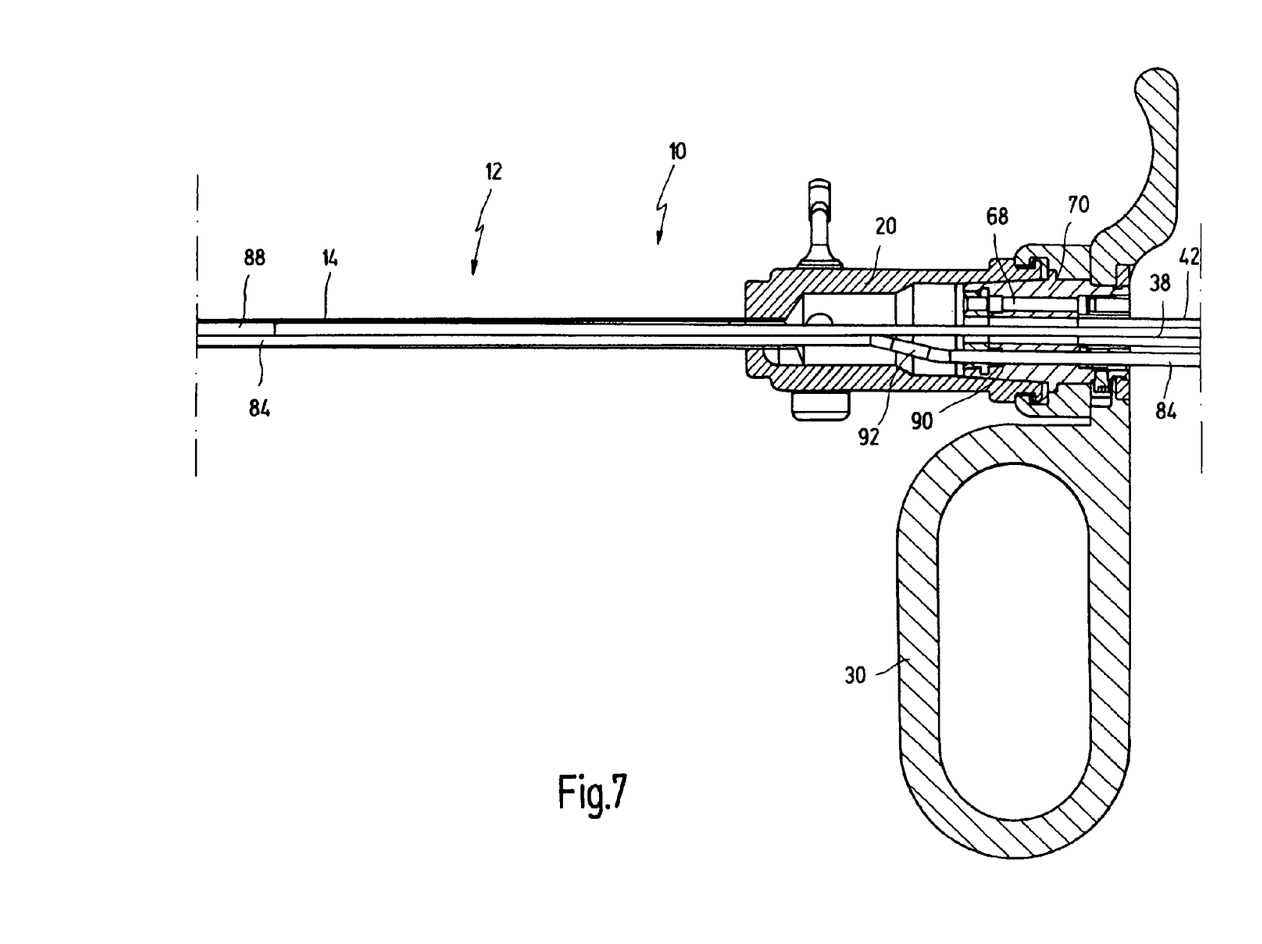
FIG. 7 shows an enlarged view, comparable to FIG. 3, of a detail of the instrument in FIGS. 5 and 6, in longitudinal section.

The work element 82 is designed in the form of a blade 86 which protrudes approximately transversely from the work element holder 84 and has roughly the shape of a sickle with a concavely curved cutting edge 87.

Except for the work element 56 and work element holder 62 being replaced by the work element 82 and work element holder 84, the instrument 10 according to FIGS. 5 to 8 is identical to the instrument 10 in FIGS. 1 to 4.

The work element holder 84 is designed as an elongate thin rod which, in contrast to the work element holder 62, does not serve as a power supply means, because the work element 82 in the form of the blade 86 operates in the manner of a scalpel without current. According to FIG. 6, the work element holder 84 is arranged parallel to the endoscope shaft 38 in the shaft 12 and is axially guided on the endoscope shaft 38 by means of a guide sleeve 88 through which the endoscope shaft 38 extends. The work element holder 84 extends through the coupling sleeve 20 and through a second bore 90 in the bush 70. Before entering the bore 90, the work element holder 84 has a kink 92. From the bushing 70, the work element holder 84 then extends, according to FIG. 8, up to the carriage 50 on which a second seat 94 is provided in which the proximal end of the work element holder 84 engages via a lock mechanism 96 and is thus secured.

Figure 8:
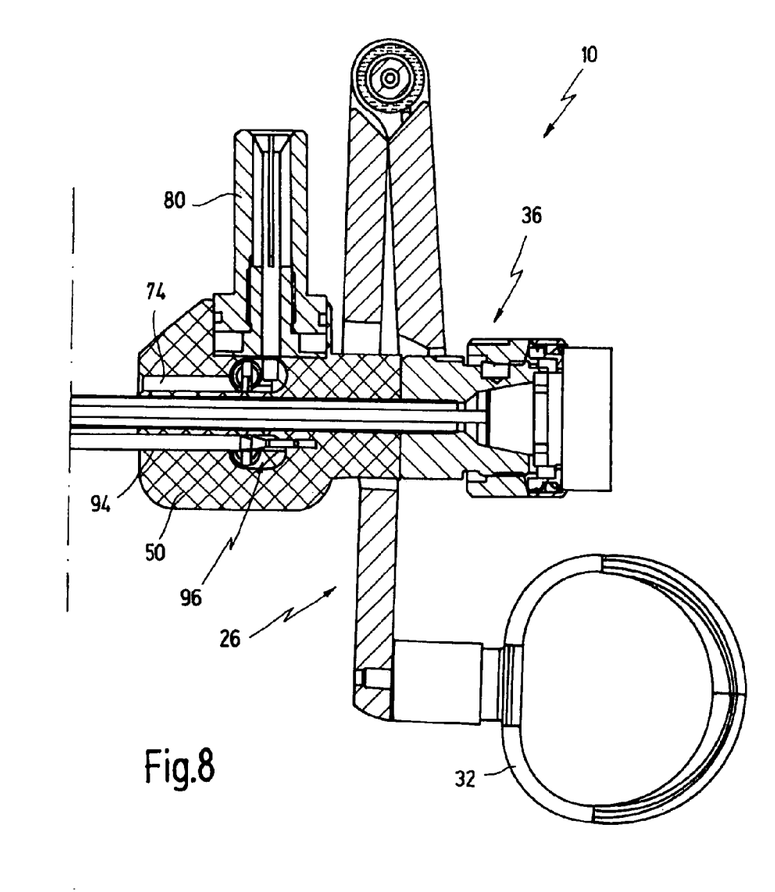
FIG. 8 shows an enlarged view, comparable to FIG. 4, of another detail of the instrument in FIGS. 5 and 6, in longitudinal section.

The second seat 94 is electrically insulated relative to the first seat 74 and does not itself have any contact arrangement for the work element holder 84. The electrical insulation of the second seat 94 relative to the first seat 74 is achieved by the fact that the body of the carriage 50 as a whole is made of plastic, the first seat 74 being provided, as described above, with metal contacts which ensure electrical contact of the first work element holder 62 and which run into the connector 80.

While the second element 82 could also be secured in the first seat 94 by means of its work element holder 84, the provision of the second seat 94 and the securing of the work element holder 84 in the seat 94, which is electrically insulated relative to the first seat 74 and itself has no electrical contacts, has the advantage of avoiding a situation where high-frequency current is conducted via the work element holder 84 and via the work element 82 to the patient or physician, specifically when the instrument 10 is connected to the high-frequency generator and the latter is not switched off.

The second seat 94 is spaced apart from the first seat 74 and is arranged below the receiving tube 42 for the endoscope when the instrument 10 is being duly used, that is to say in the position shown in FIGS. 5 to 8. In other words, the second seat 94 is located at that end of the endoscope shaft 38 directed towards the grip parts 24 to 26, or more precisely the rings 30 and 32. From the carriage to the distal end, the work element holder 84 extends below the endoscope shaft 38 and on that side of the endoscope shaft 38 directed towards the rings 30, 32, and the work element 82 in the form of the blade 86 protrudes upward from the work element holder 84, so that basically only the work element 82 is to be seen through the viewing window 64 of the endoscope. By actuation of the movable grip part 26, the second work element 82 is moved axially, as was described above for the first work element 56, and by pulling back the work element 82, the concave cutting edge 87 can be used to make a tractive cut in the tissue that is to be treated.

The lock mechanism 96 for securing the work element holder 84 in the second seat 94 is identical or similar to the lock mechanism for the first seat 74, as was already described above.

A common operating element 98 in the form of a push button is provided both for the lock mechanism 96 and for the lock mechanism 76 and, when pressed, it releases both lock mechanisms 76 and 96 simultaneously so that the respectively used work element holder 62 or 84 can be withdrawn from the carriage 50.

The instrument 10 is always only used with one work element, in the illustrative embodiment shown either with the electrosurgical work element 56 comprising the work element holder 62, or with the unpowered work element 82 comprising the work element holder 84.

The instrument 10 also has a suction and/or Irrigation attachment 100 which is connected to the coupling sleeve 20 and through which irrigation fluid can be suctioned into the hollow tube 14 in the distal direction and/or liquid and/or tissue sections can be suctioned off through the hollow tube 14.

In FIGS. 5 to 8, the suction and/or irrigation attachment 100 is shown turned through 90° about the longitudinal central axis of the shaft 12, but it will be appreciated that, in the practical application of the instrument 10, the shaft 12 has the same rotation position in the operating mode according to FIGS. 1 and 4 and in the operating mode according to FIGS. 5 to 8. The different rotation position has been chosen only for the drawing.

While only one attachment 100 is shown in the drawing, two such attachments can also be present, so that the instrument is able to perform suction and irrigation at the same time.

What is claimed is:

1. A medical instrument for treating body tissue, comprising an elongate shaft having a distal end and a proximal end, and defining a longitudinal direction, a handle arranged at said proximal end of said shaft, and having a carriage movable in said longitudinal direction, said carriage having a first seat, an elongate first work element holder having a distal end and a proximal end, a first work element being arranged at said distal end of said first work element holder, said proximal end of said first work element holder being releasably connectable with said first seat of said carriage of said handle, a receiver for receiving an endoscope having an endoscope shaft extending substantially parallel to said first work element holder, when said proximal end of said first work element holder is connected with said first seat of said carriage, wherein said carriage has at least a second seat which is spaced apart from said first seat, an elongate second work element holder having a distal end and a proximal end, said second work element holder supporting a second work element, said proximal most end of said second work element holder being releasably connectable with said second seat of said carriage of said handle, wherein said first seat of said carriage is provided with an electrical contact arrangement, and wherein said second seat of said carriage is electrically insulated relative to said first seat and is electrically insulated without having an electrical contact arrangement, such that said first work element can be electrically powered whereas said second work element may not be electrically powered, and wherein said first seat has a first lock mechanism configured for directly securing said proximal most end of said first work element holder and said second seat has a second lock mechanism configured for directly securing said proximal most end of said second work element holder, and wherein said first lock mechanism and said second lock mechanism are jointly assigned a common operating element for releasing said first and at least second work element holder.

2. The instrument of claim 1, wherein said at least second seat of said carriage is insulated relative to said first seat of said carriage by an electrically insulating plastic.

3. The instrument of claim 1, wherein said carriage as a whole is designed as a plastic body in which at least one electrical contact is present in said first seat only.

4. The instrument of claim 1, further comprising an endoscope having an endoscope shaft, wherein said receiver comprises a receiving tube, wherein said first seat and said at least second seat on said carriage are positioned such that, when said instrument is held in hand in a due manner, said first seat is located above said receiving tube for said endoscope shaft, and said at least second seat is located below said receiving tube for said endoscope shaft.

5. The instrument of claim 1 further comprising an endoscope having an endoscope shaft, wherein, when said instrument is held in hand in a due manner, said first work element holder, when secured on said carriage, extends above said endoscope shaft, and wherein said first work element protrudes downward from said first work element holder, approximately perpendicular to said longitudinal direction of said shaft.

6. The instrument of claim 5, wherein said first work element is an electrode.

7. The instrument of claim 1, further comprising an endoscope having an endoscope shaft, wherein, when said instrument is held in hand in a due manner, said at least second work element holder, when secured on said carriage, extends below said endoscope shaft, and wherein said at least second work element protrudes upward from said second work element holder, approximately perpendicular to said longitudinal direction of said shaft.

8. The instrument of claim 7, wherein said at least second work element is a blade.

9. The instrument of claim 1, wherein said shaft is releasably secured on said handle, and, when secured, said shaft surrounds at least one of said first and at least second work element holder, and said at least one of said first and second work element holder is axially movable relative to said shaft.

10. The instrument of claim 1, wherein said receiver comprises a guide tube, wherein said carriage is mounted in an axially movable manner on said guide tube, wherein said guide tube serves as a receiving tube for said endoscope shaft.

11. The instrument of claim 1, wherein said medical instrument is a resectoscope.

* * * * *